United States Patent [19]

Svanberg

[11] Patent Number: 5,197,227
[45] Date of Patent: Mar. 30, 1993

[54] DENTAL CURET AND SHARPENING MACHINE SYSTEM

[76] Inventor: Gunnar K. Svanberg, 2814 NW. 58th Blvd., Gainesville, Fla. 32606

[21] Appl. No.: 726,618

[22] Filed: Jul. 8, 1991

Related U.S. Application Data

[63] Continuation-in-part of Ser. No. 407,688, Sep. 14, 1989, Pat. No. 5,030,091, which is a continuation of Ser. No. 92,887, Sep. 4, 1987, abandoned.

[51] Int. Cl.$^5$ .............................................. B24B 9/04
[52] U.S. Cl. ........................................ 51/125; 51/220
[58] Field of Search ............... 51/109 R, 109 BS, 110, 51/121, 122, 123 R, 124 R, 125, 125.5, 126, 128, 220, 221 R, 221 BS, 234, 217 T, 217 A, 217 S, 218 R, 218 A, 218 T

[56] References Cited

U.S. PATENT DOCUMENTS

| | | | |
|---|---|---|---|
| 1,350,951 | 8/1920 | Artmaier | 51/220 |
| 2,114,757 | 4/1938 | Yerkes | 51/125 |
| 2,380,988 | 8/1945 | Mudler | 51/220 |
| 2,544,097 | 3/1951 | Lentz | 51/220 |
| 2,578,309 | 12/1951 | Kroczek | 51/125 |
| 4,535,570 | 8/1985 | Ochiai et al. | 51/123 R X |

OTHER PUBLICATIONS

Nordent Catalog No. 103, pp. 16-17, 1982.

Primary Examiner—Bruce M. Kisliuk
Assistant Examiner—John A. Marlott
Attorney, Agent, or Firm—Saliwanchik & Saliwanchik

[57] ABSTRACT

A dental curet and sharpening machine has been developed for complete mechanical guidance of the instruments during the sharpening procedure. Double-ended dental curets comprising cutting blades, shanks, and a handle have been designed so that regardless of the instrument's rake angle, the arc center of the toe on the face of the cutting blade which is to be sharpened lies on the longitudinal center axis of the instrument and at a constant distance from the reference points on the instrument handle. The sharpening machine comprises a base, an electrical motor with a rotating sharpening stone, and an instrument guide unit. The instrument guide unit can position the blade face of a curet of any rake angle in a horizontal plane with the arc center of the toe on the blade's face coincident with a vertical axis about which the guide unit is swung while the blade is engaged with the rotating stone during the cutting procedure. The invention comprises three aspects: 1) the curets; 2) the sharpening machine; and 3) the method of sharpening curets.

1 Claim, 8 Drawing Sheets

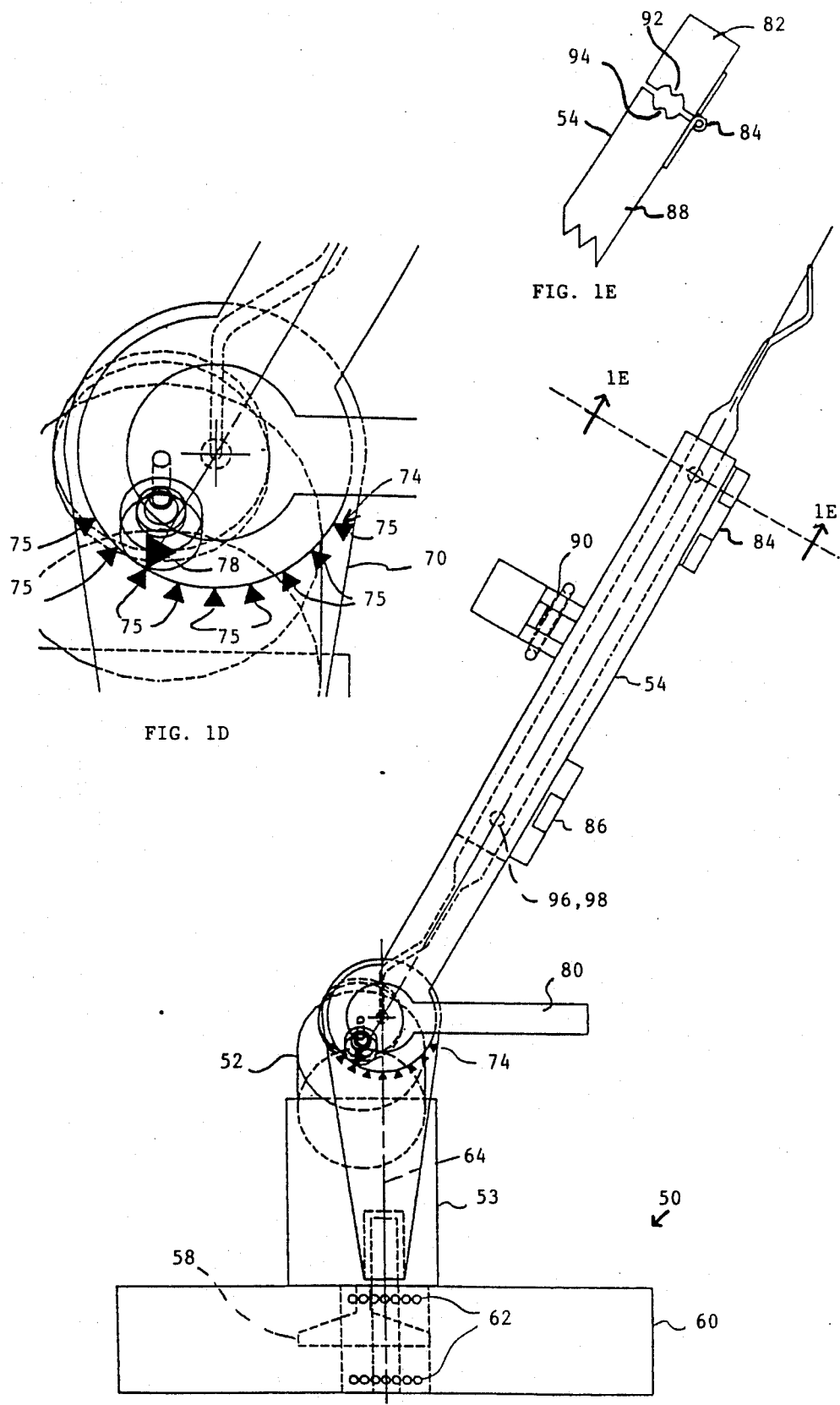

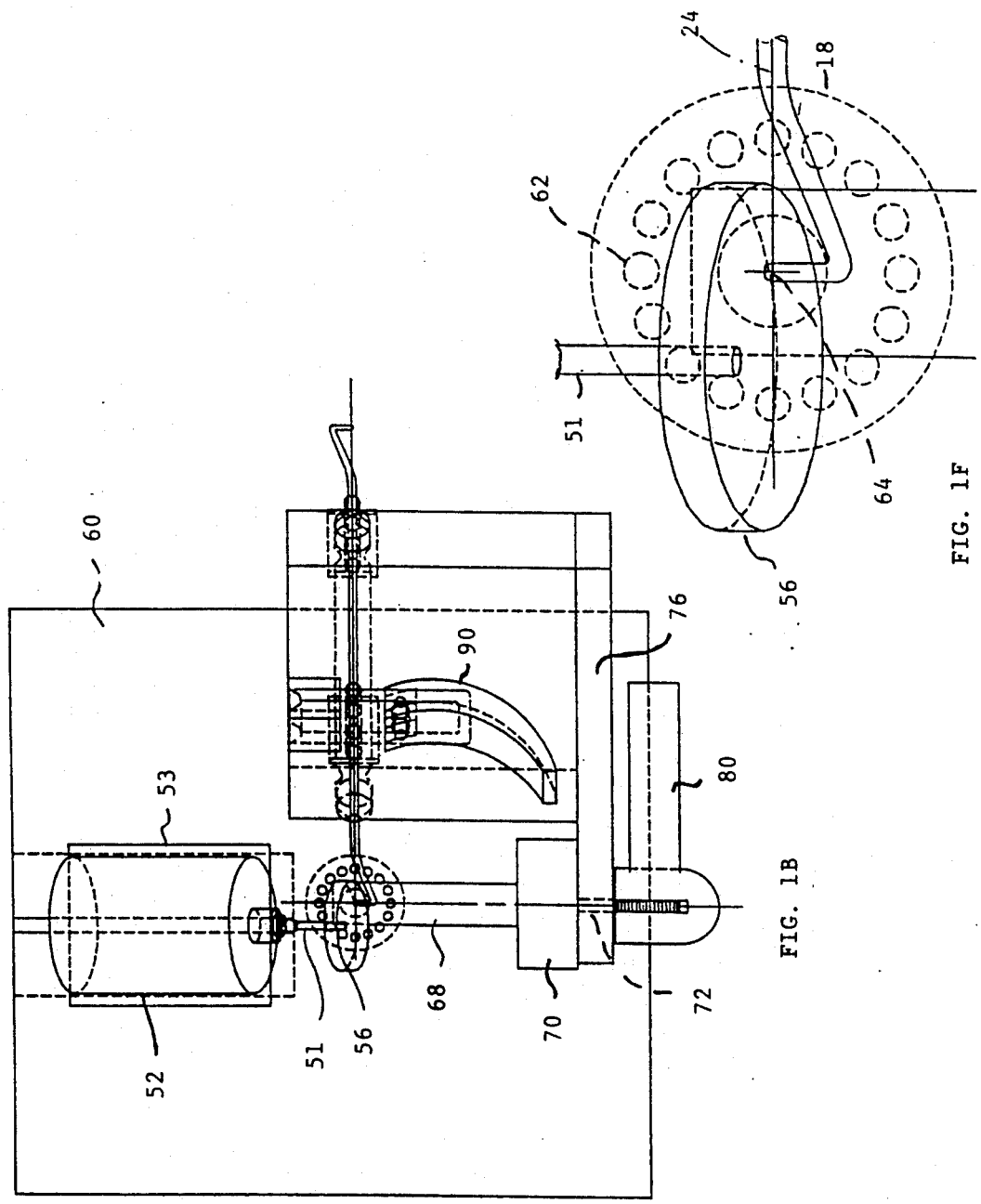

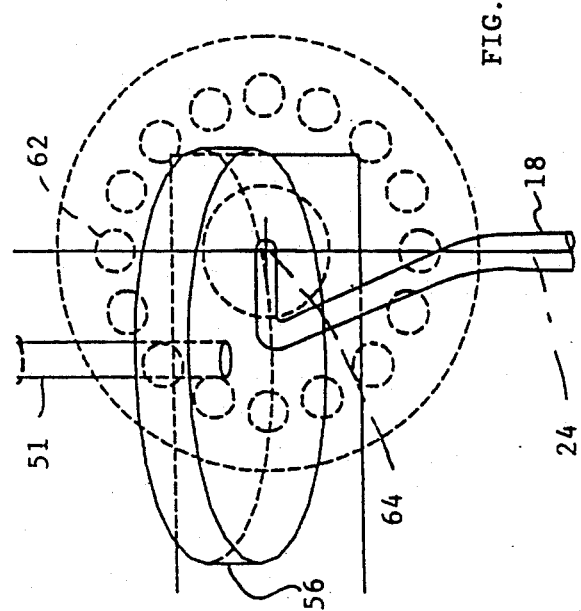
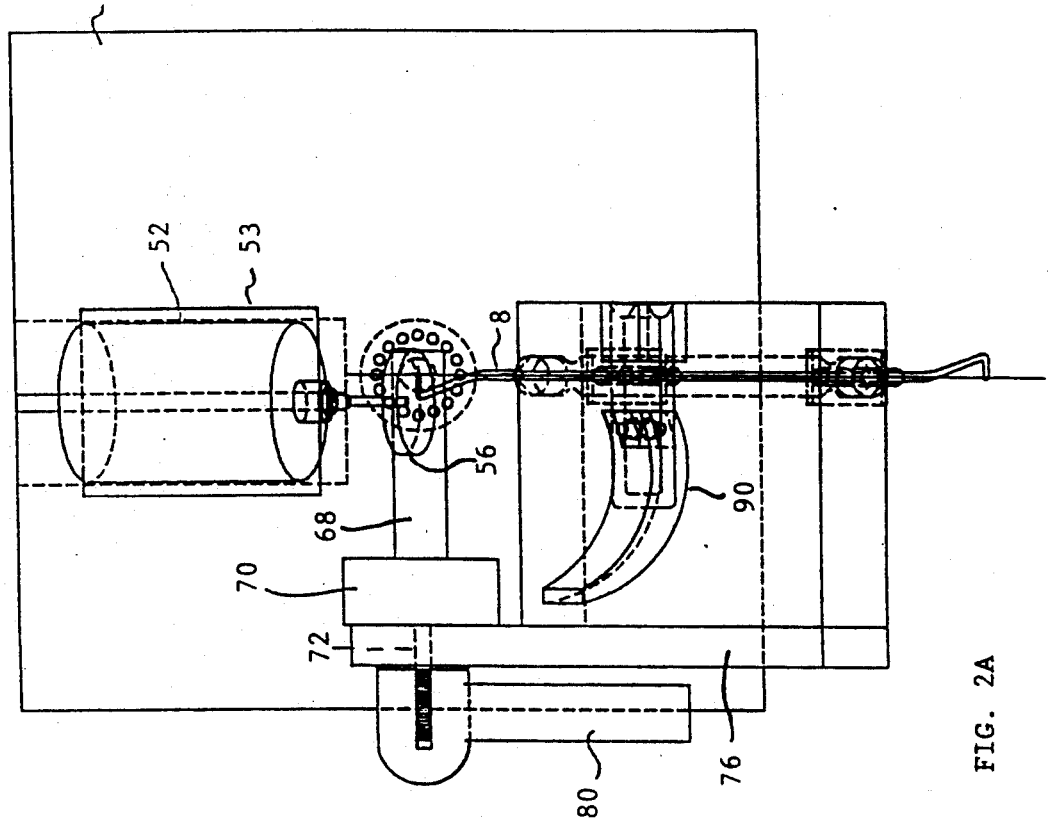
FIG. 2B
FIG. 2A

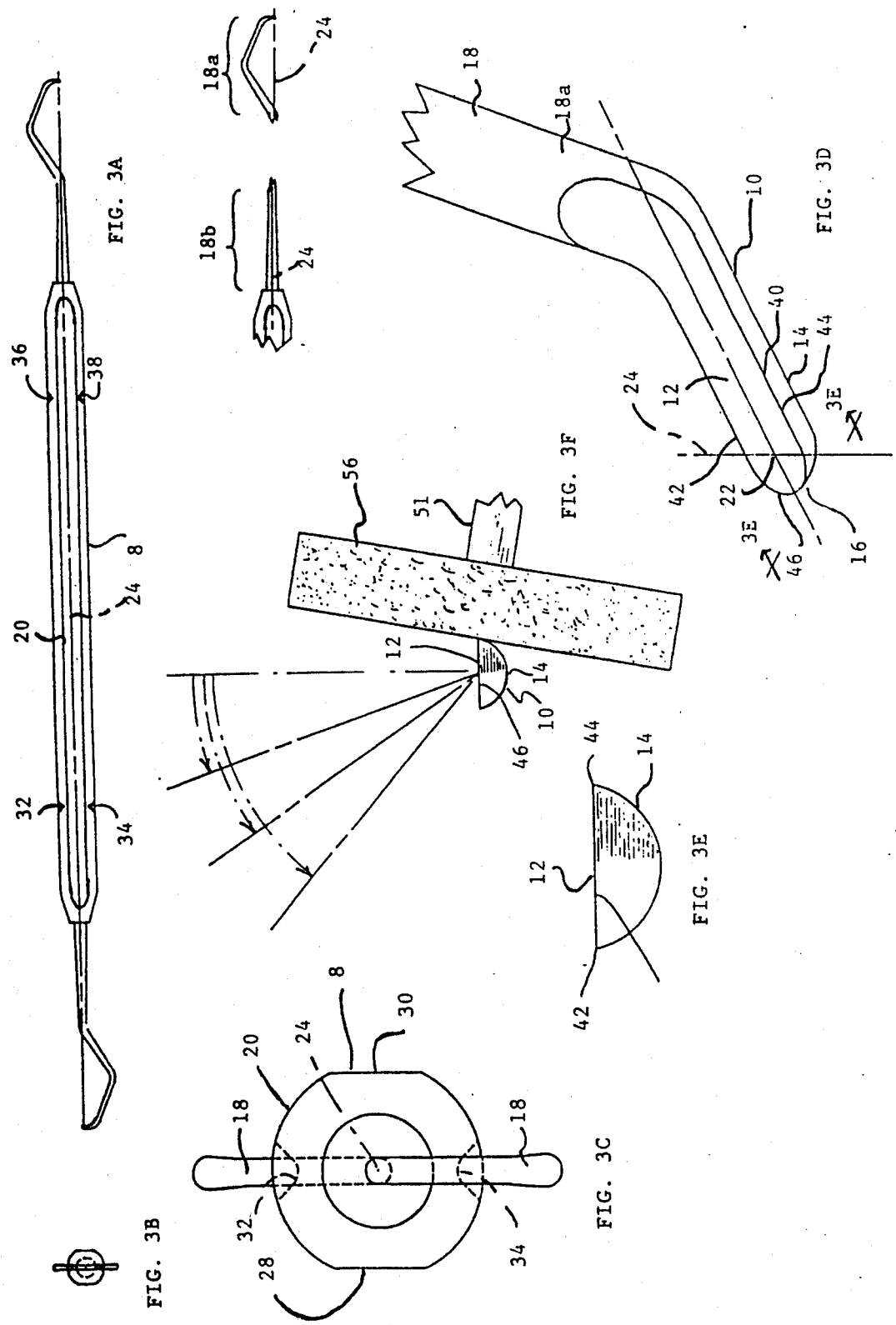

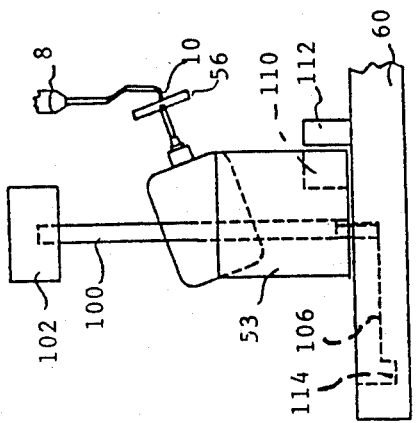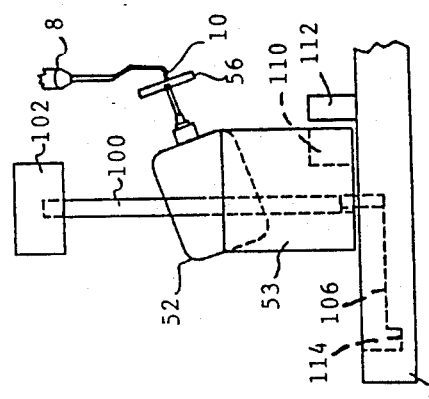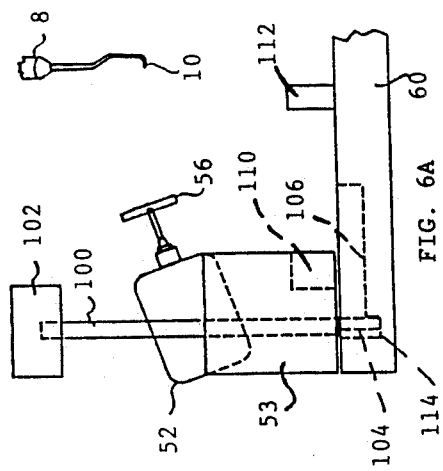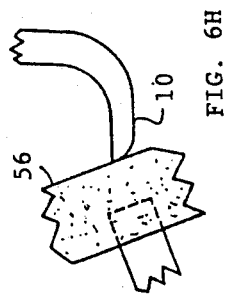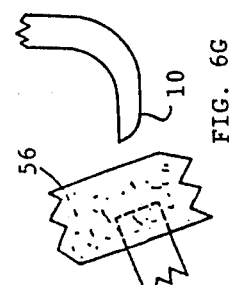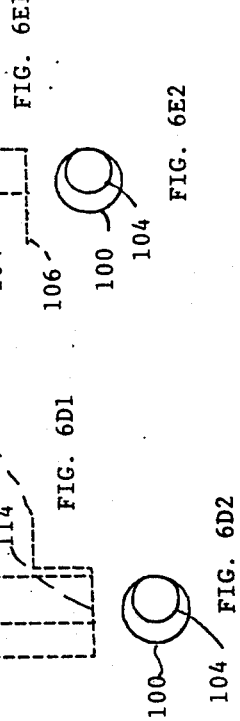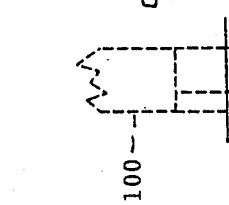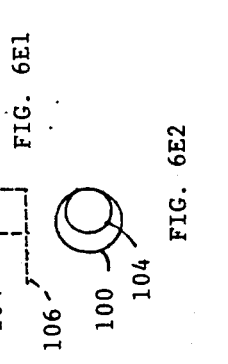

DENTAL CURET AND SHARPENING MACHINE SYSTEM

CROSS-REFERENCE TO RELATED APPLICATIONS

This is a continuation-in-part of copending application Ser. No. 07/407,688, filed Sep. 14, 1989, now U.S. Pat. No. 5,030,091, which is a continuation of application Ser. No. 07/092,887, filed Sep. 4, 1987, now abandoned.

BACKGROUND OF THE INVENTION

Scaling and root planing for the removal of calculus and contaminated root cementum are essential procedures in the treatment of periodontal diseases. For this purpose, dental curets are used for orthogonal cutting of the root surfaces, a method that removes thin chips of contaminated cementum.

This root planing procedure dulls the cutting edge of the curets which, for proper cutting action, have to be sharpened at frequent intervals. Up to now such sharpening action has been done as a free-hand procedure, with or without guide plates, resulting in edges of inferior sharpness and incorrect edge angles with serious aberrations from the ideal shape of the cutting blade.

A variety of dental curets of different shapes are available on the market, but there is no one single set of curets that in a systematic and logical way guides the operator in the selection of instruments needed for optimal efficiency in the different areas of the oral cavity.

BRIEF SUMMARY OF THE INVENTION

The invention comprises a dental curet and sharpening machine system that allows both professional and non-professional personnel to sharpen dental curets with the utmost precision.

The curets themselves are designed to provide a series of instruments with different rake angles in regular increments. The rake angle of each instrument is identified by the handle having a color code which also serves as a guide for the setting of the sharpening machine. Each instrument has two cutting blades, one at each longitudinal end. The two blades are of the same rake angle but are mirror images of each other in that one is "right-handed" and the other "left-handed."

The handles of the curets contain reference points that are in a particular relationship to the cutting blades. These reference points are used to locate the instrument in a fixture portion of the sharpening machine. In the particular example of the double-ended curet that is to be illustrated and described, the reference points are advantageously arranged in a symmetrical pattern. Specifically, four reference points are contained in the handle of the double-ended curet, and they may be considered to constitute two pairs. One pair of reference points is nearer to one blade, while the other pair of reference points is nearer to the other blade. This results in the two pairs of reference points being spaced apart from each other along the main longitudinal axis of the instrument. The two reference points of each pair are equidistant from the arc-center on the face of the nearer blade's semi-circular shaped cutting blade tip. Therefore, the two reference points are also equidistant from the arc center on the face of the farther semi-circular shaped cutting blade tip. Moreover, the two reference points of each pair are 180° apart about the longitudinal axis of the handle. However, their circumferential locations about the axis are the same so that two of the four reference points, namely one of each pair, lie on one side of the handle while the other two of four reference points, namely the other of each pair, lie on the opposite side of the handle. The longitudinal axis of the instrument passes through the arc centers on the faces of the cutting blades' semi-circular shaped tips.

The combination of these features makes it possible to sharpen curets with different rake angles by a simple adjustment of the sharpening machine as indicated by the color code. The curets are clamped in the fixture portion of the machine which is adjusted for the particular rake angle of the curet being sharpened. The machine provides complete mechanical guidance during the sharpening procedure.

A grinding stone, in the form of a wheel, is mounted on the shaft of an electric motor, which is positionable along a guide in the base of the machine. The grinding wheel is disposed at a fixed angle, which guarantees the restoration of a sharp cutting edge of the correct edge angle when the motor is positioned to bring the wheel into contact with the blade, and the fixture is swing in an arc to cause the cutting edge to be passed against the rotating wheel, first at one side of the blade, then along the semi-circular shaped tip, and finally at the other side.

The foregoing features, advantages, and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

BRIEF DESCRIPTION OF THE DRAWINGS

FIGS. 1A, 1B, and 1C are respectively a front elevational view, a top plan view, and a side elevational view of a preferred embodiment of the dental curet and sharpening machine system of the invention.

FIG. 1D is an enlarged fragmentary view of a portion of FIG. 1A; FIG. 1E is a fragmentary cross sectional view in the direction of arrows 1E—1E in FIG. 1A; FIG. 1F is an enlarged fragmentary view of a portion of FIG. 1B; and FIG. 1G is an enlarged fragmentary view of a portion of FIG. 1C.

FIG. 2A is a view similar to FIG. 1B but showing a different position; FIG. 2B is an enlarged view of a portion of FIG. 2A.

FIG. 3A is a longitudinal view of a curet shown by itself.

FIG. 3B is an end view of FIG. 3A; and FIG. 3C is an enlarged view of FIG. 3B.

FIG. 3D is a fragmentary perspective view of a curet blade.

FIG. 3E is an enlarged transverse view taken in the direction of arrows 3E—3E in FIG. 3D.

FIG. 3F is a fragmentary view in the same direction as FIG. 3E, but on a reduced scale and illustrating a step in the sharpening procedure.

FIGS. 6A, 6B, and 6C are fragmentary views illustrating a series of steps in the sharpening procedure for purposes of explanation.

FIGS. 6D1, 6E1, and 6F1 are close-up views of portions of FIGS. 6A, 6B, and 6C, respectively; and FIGS. 6D2, 6E2, and 6F2 are bottom end views of FIGS. 6D1, 6E1, and 6F1, respectively.

FIGS. 6G and 6H are close-up views of other portions of FIGS. 6B and 6C.

DESCRIPTION OF A PREFERRED EMBODIMENT

Curets

Figures 1C, 1G:
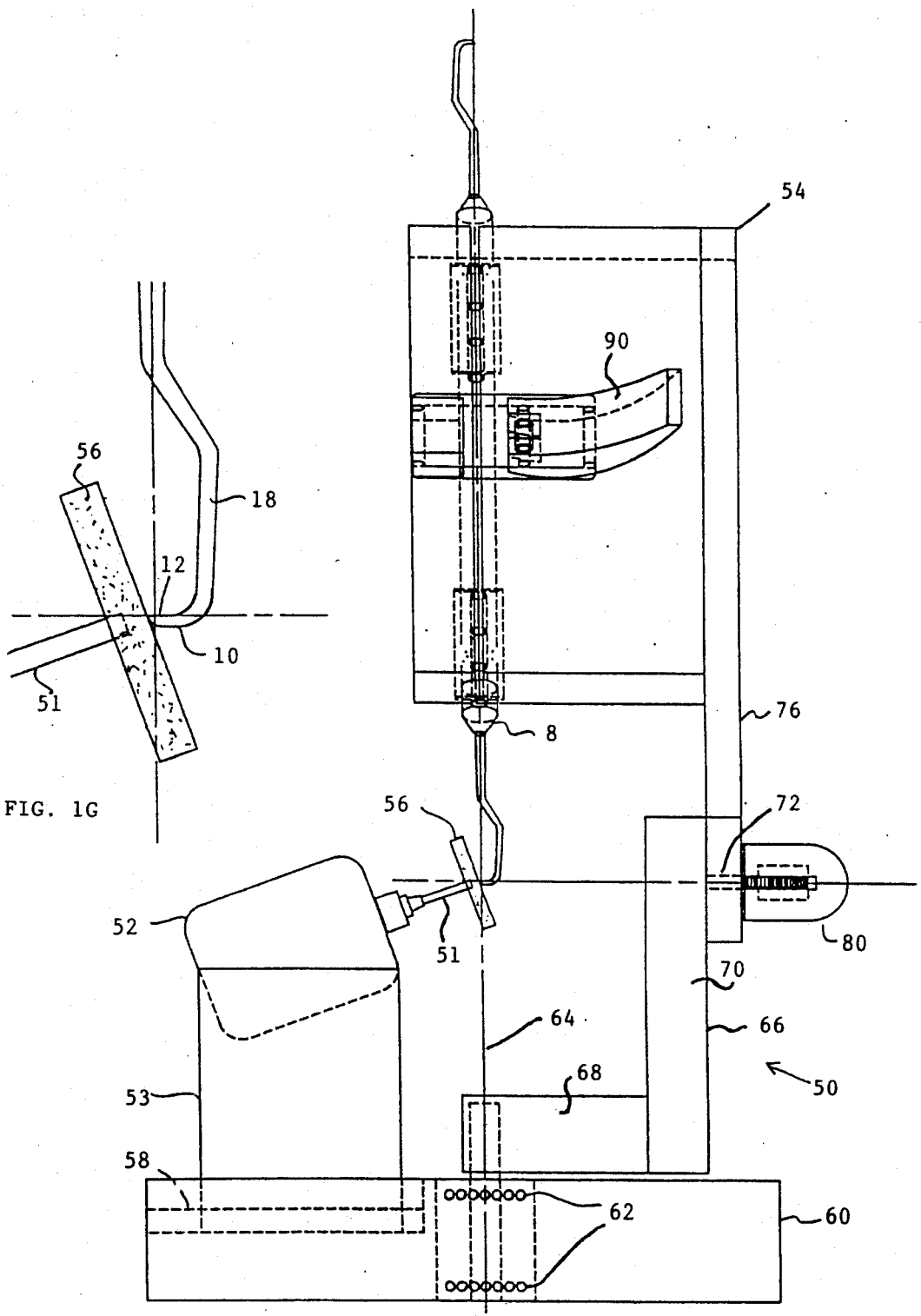
Figure 4:
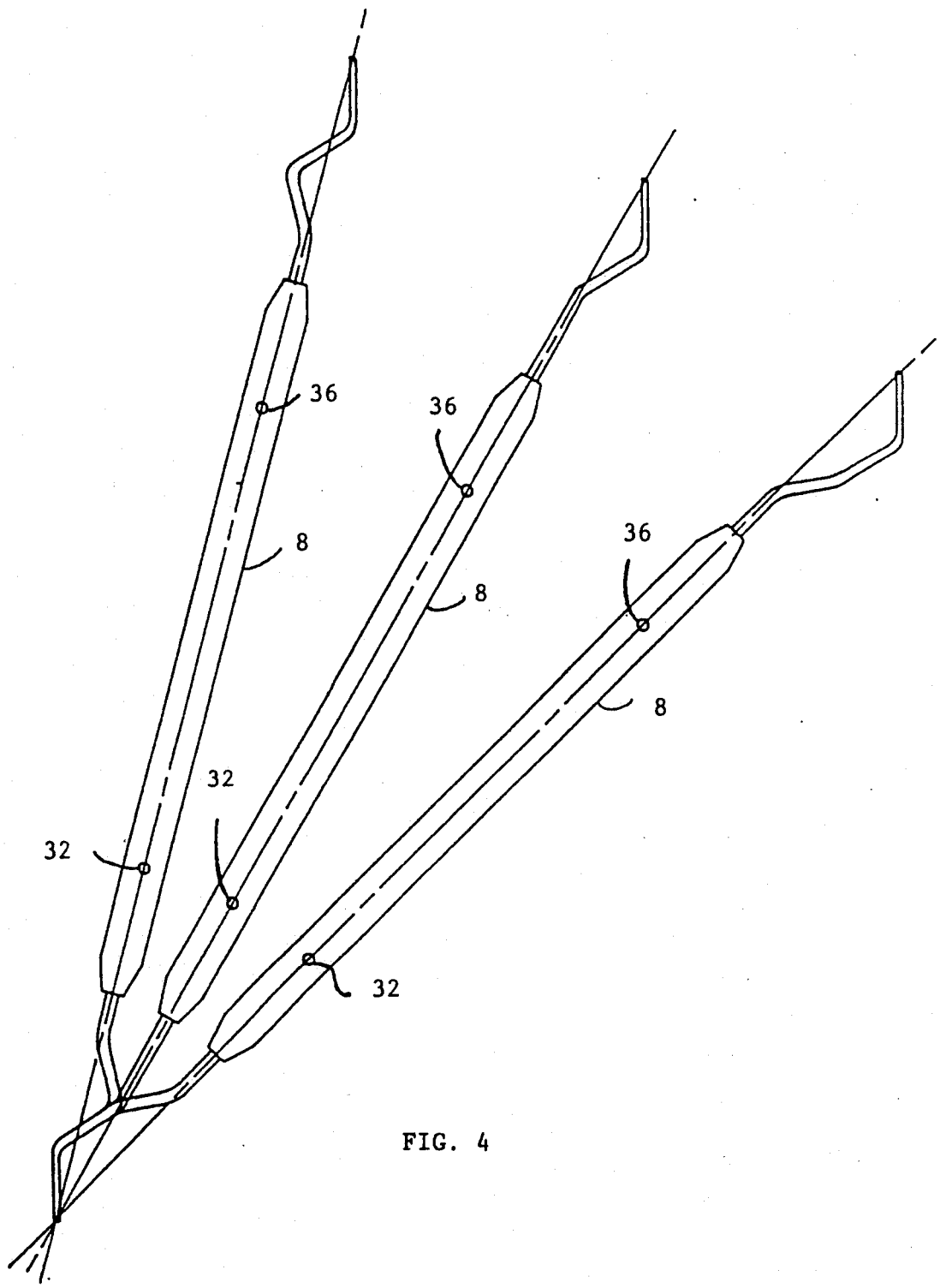
FIG. 4 is a view of three curets with different rake angles. Note that the configuration of the lower shank in the cutting blade is identical for all three instruments.

FIG. 3 shows that the cutting blade 10 of each curet 8 has a flat top surface 12 (the face), a rounded bottom surface 14 (the base), and a circular tip 16 (the toe). A shank 18, which has several bands, connects the blade to the handle 20. The curet is double-ended, i.e., has cutting blades in both ends. When viewed in working position, each blade is the other's mirror image in that the toe of one blade will point to the left whereas the other will point to the right. The shank can have various configurations, but the arc center 22 of the toe on each blade's face is always located on the longitudinal center axis 24 of the instrument, i.e., the longitudinal center axis of the handle. The configuration of the lower half 18a of the shank is identical for all instruments regardless of the instrument's rake angle, i.e., the angle between the face of the cutting blade and the long axis of the handle. The configuration of the upper half 18b of the shank determines the rake angle of the curet, and a set of curets of different rake angles facilitates access to hard-to-reach sites in the oral cavity. The upper portions of the shanks are designed to provide sets of instruments of different rake angles in regular angular increments, which are indicated by a color code on the instrument handle. FIGS. 3F and 4 show three different rake angles.

The handle 20 has a circular cross-section interrupted by two opposing flat surfaces 28, 30 along almost its entire length. These flat surfaces are parallel with the side edges of the cutting blade. The handle has four circular conical depressions 32, 34, 36, and 38, which form a symmetrical pattern of reference points for the two blades. Depressions 32, 34 constitute one pair of reference points and depressions 36 and 38 another pair. These four reference points are arranged in the manner described earlier. The four reference points are identical, both in the pattern in which they are arranged relative to the blades and in their specific details, in all curets regardless of the configuration of their shanks, i.e., regardless of rake angle.

The junction between the face 12 and the base 14 of the blade constitutes the cutting edge 40. For proper cutting action of the curet, the edge portions 42, 44 along the sides and the end edge portion 46 around the toe must be sharpened at frequent intervals. The grinding is always done on the base surface 14 of the cutting blade, never on the face, for an edge angle of about 80 degrees. It is important to maintain the proper edge angle as well as the shape of the blade, i.e., a circular toe. In order to meet all these requirements, the guide unit of the sharpening machine, to be described in the next section of the text, is designed to provide mechanical guidance for the curets during the sharpening procedure.

SHARPENING MACHINE

Refer to FIGS. 1A–1G, and 2A–2B. The sharpening machine 50 supports two units: the electric motor 52 and the instrument guide 54. The electric motor, on the shaft 51 of which is fitted a circular rotating sharpening stone 56, is disposed atop a support block 53 with the shaft at a fixed angle to the horizontal plane in order to achieve the proper edge angle of the curet's cutting blade. The motor and support block can be moved along a straight guide 58 in the base 60 of the machine toward and away from the instrument guide unit 54. It is moved away from the instrument guide unit to facilitate both the placement of the curet in the instrument guide unit before sharpening, and the removal of the curet from the instrument guide unit after sharpening. It is moved toward the instrument guide unit for the sharpening procedure.

The instrument guide unit is mounted in a ball bearing 62 housed in the base of the machine which allows the instrument guide unit to rotate in the horizontal plane about a vertical axis 64. The lower portion 66 of the instrument guide unit (the support portion) comprises one horizontal member 68 and one vertical member 70, the latter one fitted with a horizontal shaft 72 and color-coded dial 74 having a series of uniquely colored, pointed markers 75.

The upper portion 76 of the instrument guide unit (the fixture portion) rotates around the horizontal shaft 72 of the support portion, has a center line mark 78 in its lower end, and can be locked in fixed positions by means of a wing nut 80.

The fixture portion of the instrument guide unit has a lid 82 that swings around two hinges 84, 86 attached to a base 88 of the fixture portion. The opposing surfaces of lid 82 and base 88 each have a groove of semi-circular cross-section along their common longitudinal axis when the lid is closed and secured with a clamp 90, that form a tube that can securely hold and house the curet handle 20 in the fixture portion.

Proper placement of the curet is accomplished by conical pins 92, 94, 96, 98 in the lid and base of the fixture unit. The pins are arranged in a pattern matching the pattern of the reference points in the curet's handle. When the lid is clamped in a closed position, the pins fit tightly into the conical depressions 32, 34, 36, 38 in the curet handle. These reference points will guarantee a reproducible placement of the curet so that the arc center of the toe on the face of the blade to be sharpened lies on the center of the horizontal rotation axis of the fixture portion (axis of shaft 72) as well as on the center of the vertical rotation axis of the entire guide unit (axis 64).

These integrated design features of the curets and sharpening machine make it possible to place a curet of any rake angle with the face of a cutting blade, which is to be sharpened, in the horizontal plane and with the center of the toe of that blade at the same time being on the rotation axis 64 of the guide unit. This will guarantee that the sharpening procedure will give exactly the same edge angle along the entire perimeter of the cutting blade and that the shape of the cutting blade, i.e., a rounded toe, will be maintained. Each unique marker color corresponds to the color of a curet of a particular rake angle so that, when a given color curet is placed in the fixture and the corresponding marker 75 aligned with marker 78, the face of the blade being sharpened is in the horizontal plane.

The electric motor unit contains a circular rod 100 which has a knob 102 at its top end. The rod 100 passes through a hole in the motor support block, and the rod's lower end contains an eccentric 104, which is cooperatively associated with a slot 106 in base 60, and parallel with guide 58. An electromagnet 110 is housed in the motor support block and a ferrous block 112 is mounted on base 60 for cooperative association with electromagnet 110.

One embodiment of the subject invention involves the use of a computer program to direct the functions of the sharpening machine. This embodiment utilizes the same essential features of the sharpening machine as described above. However, the use of a computer program can facilitate a level of precision which is highly desirable. For example, a fully automated sharpening machine can comprise, in addition to the features described elsewhere herein, an erasable programmable read-only memory (EPROM) chip. It is within the skill of a person trained in this art to use and program the EPROM to establish a baseline position of the fixture arm (instrument guide units) holding the curet for sharpening. The necessary baseline is created by sensing and determining the friction of the curet against the sharpening wheel. The sharpening cycle can then be readily controlled in accordance with the sensed friction.

Thus, in accordance with the teachings set forth herein, one embodiment of the subject invention is a fully automated sharpening machine comprising a base, an erasable programmable read-only memory (EPROM) chip, a sliding motor with a sharpening wheel fitted with a replaceable grinding disc, and a fixture unit that secures double-ended dental curets of different rake angles in the fixture so that the face of the cutting blades of the curets are in a predetermined plane, for this model the horizontal plane, with the center of the semi-circular tip (toe) of the blade coinciding with the fixture's vertical rotation axis, and said center of the semi-circular toe on the flat face of the cutting blade situated in the horizontal rotation axis of the fixture's distal (upper) arm by means of reference units (points) on the distal arm of the sharpening machine's fixture and the curets, all reference units placed according to an integrated design pattern for the sharpening machine and the curets, the EPROM establishing a baseline position of the fixture arm holding the curets for the sharpening of the instruments by sensing and determining the friction of the curets against the sharpening wheel and then controlling the sharpening cycle.

As used herein, the term "sharpening stone" is used generically to refer to any of a number of devices for sharpening the curets. Typically, these sharpening devices will be sharpening wheels (grinding wheels) which are readily available and well known to those skilled in the art. These sharpening wheels may use a variety of sharpening surfaces which would typically consist of very fine particles such as diamond particles. The sharpening wheels may be fitted with a replaceable grinding disc to facilitate maintenance.

OPERATION

The electric motor 52 with the sharpening stone 56 is moved away (position at FIG. 6A) from the instrument guide unit 54. A curet is clamped in the instrument guide unit, and the fixture portion is rotated around the horizontal shaft 72 in order to position the face 12 of the curet blade in the horizontal plane. The amount of rotation needed is easily determined by the alignment of the mark 78 on the vertical member of the fixture portion with the particular color mark 75 on the dial 74 that matches the color of the curet handle.

The rod 100 is pulled up out of the deep section 114 of the slot 106 and the motor with the sharpening stone is moved toward the instrument guide unit, the tip of the rod sliding along the base of the slot, until stopped by the rod hitting the end of the slot 106 (FIG. 6B). At that point, the sharpening stone is very close to, but not in contact with, the curet, and the magnet 110 in the motor unit is pulling toward the metal block 112 on the instrument base. Then, the rod is rotated to relieve the rod from the wall in the slot, and the magnet will move the motor toward the instrument guide unit until the sharpening stone is in contact with one side edge of the curet's cutting blade (FIG. 6C). The motor is started and the instrument guide unit is swung 180 degrees to sharpen the edge, first at one of the side edge portions 42, next the toe edge portion 46, and finally the other side edge portion 44. The pull of the magnet provides adequate pressure of the sharpening stone upon the curet during the sharpening procedure. The circuitry is designed so that the power line to the electromagnet is routed through a rheostat, which is mounted between the base and the instrument guide unit. The magnet is supplied with maximum power when the sharpening stone is in contact with the side edges. During the rotation of the instrument guide, when the toe of the curet is in contact with the sharpening stone, less power is let through the rheostat to the electromagnet, which therefore will exert less pull. With proper design, the pressure of the sharpening stone on the curet's blade will be constant per unit length of cutting edge during the entire sharpening procedure. The motor is stopped and moved away from the curet which is then taken out of the instrument guide. Curets with the same rake angle are sharpened in sequence to minimize required adjustments of the fixture portion of the instrument guide unit for the most efficient use of the sharpening machine.

CURET USAGE

Curets are used most efficiently when the instrument handle is parallel with the long axis of the tooth, i.e., when the instrument's rake angle is similar to the actual rake angle relative to the root surface. This mode of instrumentation is feasible in the anterior regions of the oral cavity whereas, when working in the posterior regions, the instrument will be at a considerable angle to the longitudinal axis of the tooth due to interference between the instrument handle and the opposing dental arch. Consequently, instruments of different rake angles are used in different regions of the oral cavity in order to establish the optimal working rake angle for the different curets.

However, the shanks on dental curets heretofore available offer no guidance for proper angulation of the instrument relative to the longitudinal axis of the tooth to achieve the optimal working rake angle on the root surface. The innovation of this invention encompasses curets that, regardless of the instrument's rake angle, have an identical configuration of the cutting blade and lower portions of the shank, which should be positioned parallel with the root surface for optimal working rake angle.

Heretofore, dental curets have been unavailable in sets of different rake angles in regular increments, and there have been no indicators on the instruments giving the actual rake angle. Furthermore, the usually complex configuration of the shanks gives little or no guidance in positioning the curets for proper working rake angle on the root surface.

This invention presents a new concept in the design of dental curets for their compatibility with a sharpening machine providing complete mechanical guidance during the sharpening of the instruments.

CONCLUSION

The foregoing disclosure has shown a new and unique curet and sharpening machine system characterized by a system of novel dental curets, a novel method of sharpening dental curets, and a novel sharpening machine for dental curets. It provides a set of dental curets having different rake angles to facilitate scaling and root planing procedures on patients. It provides for the expeditious sharpening of dull curets of the set by a single machine, which assures the consistent restoration of a sharp edge of the correct angle while preserving the shape of the cutting blade.

Figures 5A, 5B:
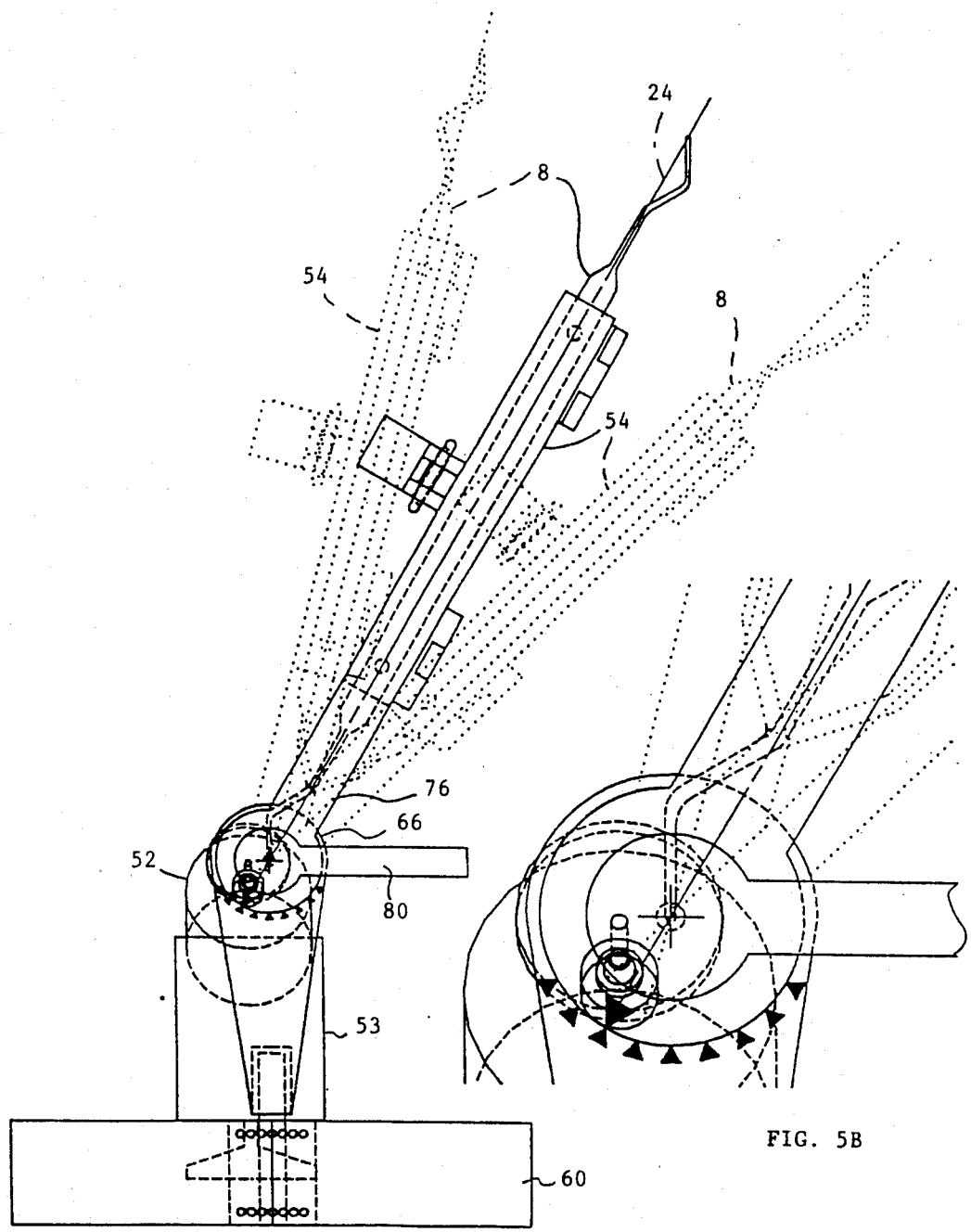
FIG. 5A is a view showing the adjustments of the fixture unit needed to put the three different curets of FIG. 4 in proper positions for the sharpening procedure.
FIG. 5B is a close-up of a portion of FIG. 5A.

Although FIGS. 1A and 1D show nine different settings for nine different rake angles, the particular number of settings and dental curets in the system may be other than this particular number. FIG. 3F illustrates only three different rake angles. Likewise, FIG. 4 shows instruments of three different rake angles and FIG. 5A shows three different settings of the machine corresponding with those three different rake angles of FIG. 4. It is to be appreciated that the relative proportions illustrated in FIG. 3D are merely representative. For example, the radius of the end edge 46 and the lengths of the side edges 42, 44 are merely representative. It is to be understood that these are merely illustrative of the general principles of the invention.

I claim:

1. A machine for sharpening any one of a series of dental curets which has a longitudinally extending handle which connects two cutting blades, each cutting blade having a face with a cutting edge formed by substantially parallel side edge portions and a substantially semi-circular distal end edge portion wherein the curets of said series differ from each other with respect to the rake angle between the face of the curet and the longitudinal axis of the handle; wherein said machine comprises the following elements:

(a) a base;
   (b) an instrument guide unit attached to said base such that said instrument guide unit may rotate about a vertical axis, said instrument guide unit comprising a fixture portion with placement means for holding a curet in a fixed position relative to said fixture portion, said instrument guide unit further comprising means for disposing said fixture portion at any one of several angles by rotating said fixture portion about a horizontal axis, the angle at which said fixture portion is disposed for a given curet is selected so that said curet face is in the horizontal plane defined by said horizontal axis;
   (c) a sharpening element movably attached to said base such that said sharpening element may be brought into contact with, or moved away from, a curet held by said placement means in said fixture portion;
   (d) a means for rotating said instrument guide about said vertical axis while said fixture portion remains at said selected angle so as to expose each edge portion of said curet face to said sharpening element, wherein said elements function together to:
   (i) place the arc center of said cutting blade's semi-circular distal end portion in said instrument guide unit's vertical rotation axis;
   (ii) place said cutting blade's face perpendicular to said instrument guide unit's vertical rotation axis; and
   (iii) place the cutting blade's face in said fixture portion's horizontal rotation axis.

* * * * *